United States Patent [19]

Greenquist

[11] 4,363,874
[45] Dec. 14, 1982

[54] MULTILAYER ANALYTICAL ELEMENT HAVING AN IMPERMEABLE RADIATION NONDIFFUSING REFLECTING LAYER

[75] Inventor: Alfred C. Greenquist, Elkhart, Ind.

[73] Assignee: Miles Laboratories, Inc., Elkhart, Ind.

[21] Appl. No.: 290,938

[22] Filed: Aug. 7, 1981

[51] Int. Cl.³ .................. G01N 33/52; G01N 33/54
[52] U.S. Cl. .......................................... 435/7; 422/56; 422/57; 435/805
[58] Field of Search .............. 422/55, 56, 57, 58; 23/230 B, 915; 435/7, 805; 424/12

[56] References Cited

U.S. PATENT DOCUMENTS

| | | | |
|---|---|---|---|
| 3,654,179 | 4/1972 | Bauer | 422/56 X |
| 3,992,158 | 11/1976 | Przybylowicz et al. | 422/57 |
| 4,042,335 | 8/1977 | Clement | 422/56 |
| 4,046,513 | 9/1977 | Johnson | 427/2 X |
| 4,050,898 | 9/1977 | Goffe et al. | 422/57 |
| 4,066,403 | 1/1978 | Bruschi | 422/57 X |
| 4,144,306 | 5/1979 | Figueras | 422/56 |
| 4,166,093 | 8/1979 | Smith-Lewis et al. | 422/56 |
| 4,168,146 | 9/1979 | Grubb et al. | 422/56 X |
| 4,255,384 | 3/1981 | Kitajima et al. | 422/56 X |
| 4,258,001 | 3/1981 | Pierce et al. | 422/56 |

*Primary Examiner*—Arnold Turk
*Attorney, Agent, or Firm*—Roger N. Coe

[57] ABSTRACT

A multilayer analytical element for detecting a ligand in or the ligand binding capacity of a liquid sample of the type having a reagent layer(s) incorporating reagents which are responsive to the ligand in or the ligand binding capacity of the sample to give a detectable response, a radiation reflecting layer, and a support layer, the improvement wherein the reagent layer(s) is a radiation diffusing layer and the radiation reflecting layer is a radiation nondiffusing reflecting layer which is (a) interposed between the reagent layer(s) and the support layer; (b) impermeable to the ligand, reagents of the reagent layer(s), and products of their interreaction; and (c) inert to the ligand, reagents of the reagent layer(s), and products of their interreaction.

29 Claims, 4 Drawing Figures

MULTILAYER ANALYTICAL ELEMENT HAVING AN IMPERMEABLE RADIATION NONDIFFUSING REFLECTING LAYER

BACKGROUND OF THE INVENTION

1. Field of the Invention

The present invention relates to the field of analytical test elements and methods, such as are useful in manual and automated diagnostic systems, and, more particularly, to multilayer analytical elements useful in the qualitative and quantitative determination of body fluid constituents and medicaments present in such body fluids.

2. Brief Description of the Prior Art

Test devices in the form of test strips and similar solid state analytical elements have become commonplace in the analysis of various types of samples, particularly biological fluids. Test strips designed for detecting clinically significant substances in biological fluids, such as serum and urine, have been advantageous in the diagnosis of disease.

Test strips of various types have been known and used for many years in a wide variety of fields, from the most familiar pH test paper devices to in vitro diagnostic devices for the detection of various urine and blood components such as glucose, protein, occult blood and so forth (e.g., as described in U.S. Pat. Nos. 3,164,534; 3,485,587; and 3,012,976). Reagent compositions found in such test strips, often having limited sensitivity, interact with the constituent or constituents to be determined by direct chemical reaction and are applied to the detection of substances that are present in liquid samples at concentrations in the millimolar range or above.

(a) Multilayer Analytical Elements

A basic multilayer integral analytical element is described in U.S. Pat. No. 3,092,465. Such multilayer elements use an absorbent fibrous carrier impregnated with one or more reagents, typically including a color former, over which is coated a semi-permeable membrane. Upon contact with a test liquid, analyte passes through the membrane and into the fibrous carrier to generate color in an amount related to the concentration of analyte. The membrane prevents passage and absorption of certain interfering components such as red blood cells, that could impair accurate reading of the color provided as a test result.

Other multilayer integral analytical elements are described in U.S. Pat. No. 3,992,158. Such elements can receive a liquid sample and spread the sample within a spreading layer of the element to obtain in the element a apparent uniform concentration of analyte, other appropriate sample constituent or analyte product and produce in the presence of analyte an analytical result that can be measured quantitatively by automated devices, using techniques such as spectrophotometry, fluorimetry, etc. Such elements can include spreading layers and reagent layers that contain a reactive or otherwise interactive material that, by virtue of its activity, promotes in the element a radiometrically detectable change, such as a color change.

U.S. Pat. No. 4,042,335 relates to an element having (1) a reagent layer which reacts with the analyte to form a diffusible, detectable species; (2) a nonfibrous radiation blocking layer, permeable to the detectable species and having an opacifying agent; and (3) a nonfibrous, radiation-transmissive registration layer in which the detectable species is detected. The element is, thus, read from below.

U.S. Pat. No. 4,006,403 (Re 30,267) relates to an element including (1) a reagent which reacts with the analyte to produce a decomposition product; and (2) a reagent which reacts with the decomposition product or an intermediate to provide a detectable change, and having, as an improvement, a barrier composition separating reagent (1) from reagent (2), and being substantially uniformly permeable to the decomposition product and substantially impermeable to interferants. Therefore, what this does is add a "filtering" layer between the "reagent" layer and the "registration" layer.

U.S. Pat. No. 4,144,306 relates to an element in which the reagent layer contains a nondiffusible material including a preformed, detectable moiety which is released and becomes diffusible in the presence of the analyte. The registration layer receives the diffusible species. Layers within the element are composed such that the preformed, detectable moiety released from the reagent layer can be detected selectively within the element.

U.S. Pat. No. 4,166,093 relates to an element having (1) a radiation-transmissive reagent layer that reacts with an analyte to provide a detectable species, and a porous radiation-blocking layer which is permeable to the analyte. As an improvement, it also has a radiation-transmissive, detectable species migration-inhibiting layer between the reagent layer and the porous radiation-blocking layer. The migration-inhibiting layer is permeable to the analyte and inhibits the migration of the detectable species to the radiation-blocking layer.

(b) Specific Binding Assay Device

Solid phase test devices have been applied to heterogeneous specific binding assays in attempts to overcome the inconveniences and disadvantages of the requisite separation step. A commonly used solid phase device of this type comprises a nonporous surface, such as the interior surface of a test tube or other vessel, to which antibody is affixed or coated by adsorption or covalent coupling. U.S. Pat. Nos. 3,826,619; 4,001,583; 4,017,597; and 4,105,410 relate to the use of antibody coated test tubes in radioimmunoassays. Solid phase test devices have also been used in heterogeneous enzyme immunoassays (U.S. Pat. Nos. 4,016,043 and 4,147,752) and in heterogeneous fluorescent immunoassays (U.S. Pat. Nos. 4,025,310 and 4,056,724; and British Pat. No. 1,552,374).

The use of such heterogeneous specific binding assay test devices is exemplified by the method of U.S. Pat. No. 4,135,884 relating to a so-called "gamma stick". The test device is incorporated with the antibody reagent and is brought into contact with the liquid sample and with remaining reagents of the reaction system, principally the label conjugate. After an incubation period, the solid phase device is physically removed from the reaction solution and the label is measured either in the solution or on the test device.

Similar devices where the antibody reagent is entrapped in a matrix such as a gel or paper web are described in U.S. Pat. Nos. 3,925,017; 3,970,429; 4,138,474; 3,966,897; 3,981,981 and 3,888,629 and in German OLS No. 2,241,646. Likewise, devices for use in heterogeneous specific binding assays wherein the antibody reagent is fixed to a matrix held in a flowthrough column are known. (U.S. Pat. Nos. 4,036,947; 4,039,652; 4,059,684; 4,153,675; and 4,166,102). The test device is usually incorporated with less than all of the necessary reagents for carrying out the assay and is merely a means for rendering the necessary separation step more convenient.

Finally, heterogeneous specific binding assay test devices have been described wherein most or all of the necessary reagents are incorporated with the same carrier element, and wherein reagent/sample contacts and separation of the free- and bound-phases are accomplished by capillary migrations along the carrier element (U.S. Pat. Nos. 3,641,235; 4,094,647 and 4,168,146). The devices described in such patents are generally considered difficult to manufacture and susceptible to irreproducibility due to the complex nature of the many chemical and physical interactions that take place along the carrier element during performance of an assay. Yet another approach to a heterogeneous immunoassay element is exemplified by U.S. Ser. No. 973,669, now U.S. Pat. No. 4,258,001, published as European patent application 13 156.

The application of homogeneous specific binding assay reagent systems to solid state test devices would provide great advantages to the routine user of such assay systems. The determination of ligands appearing in very low concentrations in liquid samples would be simplified to the steps of contacting the device with the sample and measuring, either by visual observation or by instrumental means, the resulting signal. Reagents would be provided in a solid form, with no need to store, dispense or mix liquid reagents as required when using the prior art test kits. Solid state devices would also be much more adaptable to automation than the prior art liquid systems.

British Pat. No. 1,552,607, commonly assigned herewith, describes homogeneous specific binding assay systems employing various novel labels, including chemiluminescent labels, enzyme substrate labels and coenzyme labels. At page 23, line 12 et seq of this patent there is the suggestion to incorporate the assay reagents with various carriers including liquid-holding vessels or insoluble, porous, and preferably absorbent matrices, fleeces, or flocks; gels; and the like. This lacks a detailed teaching of how to apply homogeneous specific binding assay reagent systems to solid state test devices.

German OLS No. 2,537,275 describes a homogeneous specific binding assay reagent system and poses the possibility of using slides or strips incorporated with antibody in performing the assay. In this suggestion, the label conjugate would first be mixed with the sample and thereafter the antibody incorporated test device contacted with the reaction mixture. After a suitable incubation time, it is proposed that the test device would be rinsed with buffer, dried, and then the signal (fluorescence) measured. Thus, this German OLS poses a test device and assay method much like those already known for heterogeneous specific binding assay techniques wherein the test device is immersed in the liquid reaction mixture, incubated, thereafter removed, washed, and finally read. Additionally, the proposed test device does not incorporate all of the binding assay reagents with the carrier element. Specifically, only the antibody is proposed to be incorporated with the carrier element, the label conjugate being separately added to the sample under assay prior to contact with the proposed test device.

Copending U.S. Ser. No. 255,521, filed on Apr. 20, 1981, and commonly assigned herewith, discloses a method for determining the presence of a ligand in or the ligand binding capacity of a liquid test sample, the method comprising the steps of (1) adding to the liquid sample a label conjugate comprising the ligand, or a binding analogue thereof, chemically bound to a label, (2) contacting the sample with a test device comprising a carrier matrix incorporated with reagents which, when combined with the label conjugate, produce a homogeneous specific binding assay system which produces a detectable response which is a function of the presence of the ligand or the ligand binding capacity, thereby producing the response, and (3) measuring the response.

Copending U.S. Ser. No. 202,378, filed on Oct. 30, 1980, and commonly assigned herewith, discloses a homogeneous specific binding assay device, a method for its preparation, and a method for its use in determining a ligand in or the ligand binding capacity of a liquid sample. This includes, for example, a test device for determining a ligand in or the ligand binding capacity of a liquid sample, comprising (a) reagents for a homogeneous specific binding assay system which produces a detectable response that is a function of the presence of the ligand in or the ligand binding capacity of the sample, and (b) a solid carrier member incorporated with the reagents.

Copending U.S. Ser. No. 253,147, filed on Apr. 10, 1981, and commonly assigned herewith, discloses a homogeneous specific binding assay device for use in determining a ligand in a liquid sample, comprising (a) a reagent composition including a complex of (i) a label conjugate comprising a label component coupled to the ligand or a specific binding analog thereof, and (ii) a specific binding partner for the ligand, the label providing a detectable response, or interacting with a detectant system to provide a detectable response, which is different when the label conjugate is bound by the binding partner compared to when it is not so bound and (b) a carrier incorporated with the complex.

SUMMARY OF THE INVENTION

Problems which exist in prior art elements have been recognized and are avoided, reduced, or overcome by the multilayer analytical element of the present invention. Blocking layers used in prior art elements are required to be permeable to the ligand, reagents of the reagent layer, or products of their interreaction since the response of the element is read from the element surface away from the reagent layer, i.e., the support layer surface.

The problem is that elecromagnetic radiation, such as emitted in reflectance and fluorescence systems, is affected by support layers, such as polystyrene or polyester layers, through which it must pass in these prior art elements. A portion of the electromagnetic radiation, such as light, which passes through the support layer is trapped inside the layer. As such, the amount of electromagnetic radiation, such as light, which is detected does not precisely indicate the amount resulting from the reaction which has occured in the element. Dose response results and the like therefore do not entirely represent the amount of electromagnetic radiation from the response to the ligand in the reagent layer. In the case of elements read using fluorescence systems, a constant amount of emitted light is trapped and so this problem has a more pronounced effect on the reliability of results at low ligand concentrations. In the case of elements read using reflectance systems, the problem is more severe at high ligand concentrations.

These problems are avoided, reduced, or overcome in the multilayer analytical element of the present invention. In having overcome these problems, the element of the invention emits an enhanced electromagnetic response, or signal, as compared to prior art elements. Even more notably, the ratio of signal radiation (S) to background radiation (B) emitted is enhanced, in that interfering background radiation is avoided as is demonstrated in the examples, infra.

Thus, in accordance with the present invention, there is provided a multilayer analytical element for detecting a ligand in or the ligand binding capacity of a liquid sample of the type having a reagent layer(s) incorporating reagents which are responsive to the ligand in or the ligand binding capacity of the sample to give a detectable response, a radiation nondiffusing reflecting blocking layer, and a support layer, the improvement wherein the reagent layer(s) is a radiation diffusing layer(s) and the radiation nondiffusing reflecting layer is (a) interposed between the reagent layer(s) and the support layer; (b) impermeable to the ligand, reagents of the reagent layer(s), and products of their interreaction; and (c) inert to the ligand, reagents of the reagent layer(s), and products of their interreaction.

DESCRIPTION OF THE PREFERRED EMBODIMENTS

Figure 1:
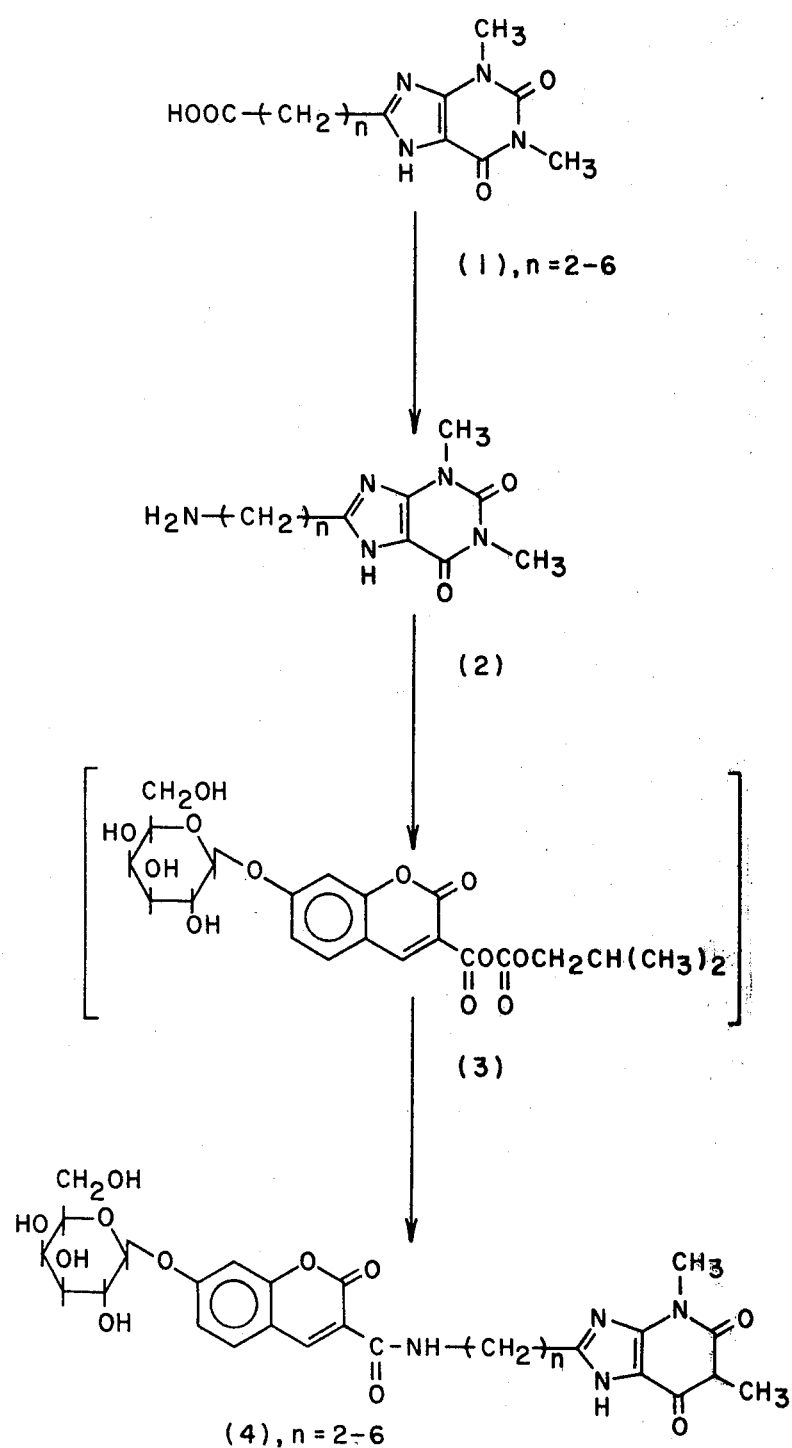
FIG. 1 is a representation of the procedure for preparing the conjugate used in Example I.

Although specific terms are used in the following description for clarity, they refer only to the particular embodiment of the invention selected for illustration, and do not limit the scope of the invention.

1. LIGAND

The term ligand is used to refer to body fluid constituents and medicaments or other substances present in such body fluids. The following exemplifies a number of such possible ligands.

The present assay element may be applied to the detection of any ligand for which there is a specific binding partner and, conversely, to the detection of the capacity of a liquid medium to bind a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein or molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinnin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglubulin, $\beta$-lipoprotein, erythropoietin, transferrin, homopexin, fibrinogen, the immunoglubulins such as IgG, IgM, IgA, IgD, and IgE, and their fragments, e.g., $F_c$ and $F_{ab}$, complement factors, prolactin, blood clotting factors such as fibrinogen, thrombin and so forth, insulin, melanotropin, somatotropin, thyrotropin, follicle stimulated hormone, leutinizing hormone, gonadotropin, thyroid stimulating hormone, placental lactogen, intrinsic factor, transcobalamin, serum enzymes such as alkaline phosphates, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones includes thyroxine and triidothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilmicin, penicillin, tetracycline, terramycin, chloromycetin, and actinomycetin; nucleosides and nucleotides such as adenosine diphosphate (ADP), adenosine triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digoxin, digitoxin, and adrenocortical steroids; and other such as phenobarbital, phenytoin, primidone, ethosuximide, carbamazepine, valproate, theophylline, caffeine, propranolol, procainamide, quinidine, amitryptilane, cortisol, desipramine, disopyramide, doxepin, doxorubicin, nortryptiline, methoxrexate, imipramine, lidocaine, procainamide, N-acetylprocainamide, the amphetamines, the catecholamines, and the antihistamines.

The liquid medium to be assayed can be a naturally occurring or artificially formed liquid suspected to contain the ligand, and usually is a biological fluid or a dilution thereof. Biological fluids that can be assayed include serum, plasma, urine, saliva, and amniotic and cerebrospinal fluids,

2. RADIATION REFLECTING LAYER

The position of the reflecting layer, relative to the reagent layer(s) and support layer, is critical to the present invention. The characteristics of the reflecting layer arise from the constituents with which it is prepared and these characteristics are, likewise, critical to the invention. Additionally, the reagent layer(s) are radiation diffusing in nature, as more fully described layer, the improvement obtained being the effect of the combination of the particular type of reflecting and reagent layers used in the invention.

The radiation reflecting layer of the invention is a radiation nondiffusing reflecting layer which is interposed between the reagent layer(s) and the support layer. It is in direct contact with one surface of the reagent layer(s) and the signal emitted from the reagent layer(s) is read from the other surface of the reagent layer(s). As such, the radiation signal is not required to pass through any layer or material for detection other than the reagent layer from which it is emitted. The characteristics or properties of the radiation reflecting layer are that it is a radiation nondiffusing reflecting layer which is both impermeable and inert to the ligand, reagents of the reagent layer(s), and products of their interreaction.

The radiation nondiffusing reflecting layer of the invention can be, for example a reflective material coated on the support layer, a reflective metal foil, or a reflective metalized tape or film. A suitable metallic coating of a support can be obtained by known electrocoating methods. Suitable reflective metal foils include Reynolds Wrap aluminum foil (Reynolds Metals Co., Richmond, Va.) which can be fixed to other layers by double-faced adhesive tape. Preferred is the use of reflective metalized tape or film, such as metalized Mylar polyester tape (3M Company, St. Paul, Minn.). In whichever embodiment is used it is especially preferred that the surface of the reflecting layer which faces the reagent layer be a mirrored surface.

3. HOMOGENEOUS SPECIFIC BINDING ASSAYS

Reagents for any homogeneous specific binding assay system may be incorporated in the present test device. In general, homogeneous specific binding assay techniques are based on the special interaction between (1) a conjugate of a binding component and a label and (2) a binding partner to the binding component in the conjugate, whereby to characteristic of the label is different when the label conjugate is bound by the binding partner compared to when such conjugate is not so bound. The affected characteristic of the label may be of any measurable nature, for instance, a chemical or physical quality of the label. In some cases, the affected characteristic is a chemical reactivity in a predetermined reaction which involves the formation or breaking of chemical bonds, covalent or noncovalent. In other cases, the affected characteristic is a physical characteristic of the label which can be measured without chemical reaction.

In the majority of cases, the present test device will incorporate homogeneous specific binding assay reagents which interact with the ligand in or its binding capacity of the sample in an immunochemical manner. That is, there will be an antigen-antibody or hapten-antibody relationship between reagents and/or the ligand or its binding capacity in the sample. Such assays therefore are termed immunoassays and the special interaction between the label conjugate and its binding partner is an immunochemical binding. Thus, in such instances, the binding component of the label conjugate is an antigen, hapten or antibody (or a fragment thereof) and the binding partner is its corresponding immunochemical binding partner. However, it is well understood in the art that other binding interactions between the label conjugate and the binding partner serve as the basis of homogeneous specific binding assays, including the binding interactions between hormones, vitamins, metabolites, and pharmacological agents, and their respective receptors and binding substances.

Where the sample is being assayed to determine the presence or amount of a particular ligand therein, the reagents for the homogeneous specific binding assay technique comprise, in the usual case, (1) a label conjugate composed of the ligand, or a binding analog thereof, chemically coupled to the label, (2) a binding partner for the ligand, e.g., an antibody or fragment thereof, a natural receptor protein, and the like, and (3) any ancillary reagents necessary for measuring the labeling substance in the label conjugate. A limiting amount of the binding substance is introduced so that any ligand in the sample will compete with the label conjugate for binding to the binding partner. The distribution of the label between the bound-species and the free-species will therefore determine the magnitude of the detectable response from the label, which in turn will be a function of the presence of the ligand. Another scheme for determining a ligand is presented where the label conjugate is composed of a labeled binding partner of the ligand and upon binding to the ligand the label is affected in terms of its detectable response. Where ligand binding capacity of the sample is under assay, the label conjugate will be composed of the ligand, or a binding analog thereof, chemically coupled to the label whereby the capacity of the sample to bind the label conjugate, such as due to the presence of a binding partner of the ligand in the sample, determines the effect made on the detectable signal from the label.

Several different homogeneous specific binding assay systems are known in the art, and the following are examples, without limiting the scope of the present invention, of some such systems contemplated for use in the present test device. The following systems are listed according to the nature of the label used.

(a) Enzyme Prosthetic Group Labels

In this system, the label is a prosthetic group of an enzyme, and the ability of a catalytically inactive apoenzyme to combine with the prosthetic group label to form an active enzyme (holoenzyme) is affected by binding of the label conjugate with its binding partner. Resulting holoenzyme activity is measurable by conventional detectant systems to yield an ultimate detectable signal. Assay systems of this type are described in commonly assigned, copending application Ser. No. 45,423, filed June 4, 1979, now U.S. Pat. No. 4,238,565, (corresponding to published British Pat. No. 2,023,607). A particularly preferred prosthetic group-labeled assay scheme employs flavin adenine dinucleotide (FAD) as the label and apoglucose oxidase as the apoenzyme. Resulting glucose oxidase activity is measurable by a colorimetric detectant system comprising glucose, peroxidase, and an indicator system which produces a color change in response to hydrogen peroxide.

In this preferred assay scheme, the FAD-label conjugate is preferably of the formula:

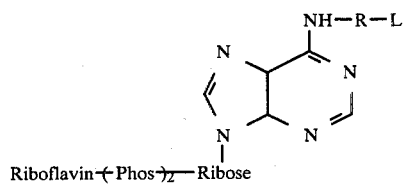

wherein Riboflavin (Phos)$_2$ Ribose represents the riboflavin-pyrophosphate-ribose residue in FAD, R is a linking group, and L is the binding component, e.g., the ligand or analog thereof.

(b) Enzyme Substrate Labels

In this system, the label is selected so that the label conjugate is a substrate for an enzyme and the ability of the enzyme to act on the substrate-label conjugate is affected, either in a positive or negative sense, by binding of the label conjugate with its binding partner. Action of the enzyme on the substrate-label conjugate produces a product that is distinguishable in some feature, usually a chemical or physical feature such as chemical reactivity in an indicator reaction or such as a photometric character, e.g., fluorescence or light absorption (color). Assay systems of this type are described in commonly assigned, copending applications Ser. Nos. 894,836, filed Apr. 10, 1978 (corresponding to published German OLS 2,618,511) and 87,819, filed Oct. 23, 1979, now U.S. Pat. No. 4,279,992; and in Anal. Chem. 48:1933(1976), Anal. Biochem. 77:55(1977) and Clin. Chem. 23:1402 (1977).

A particularly preferred substrate-labeled assay scheme employs a label conjugate of the structure

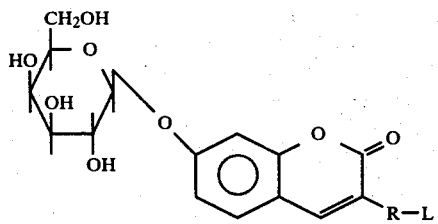

wherein R is a linking group and L is the binding component, e.g., the ligand or analog thereof, whereby the ability of the enzyme β-galactosidase to cleave the conjugate yielding a product distinguishable by its fluorescence is inhibited by binding of the conjugate with its binding partner.

(c) Coenzyme Labels

The label conjugate in this system is composed, in its label portion, of a coenzyme-active functionality, and the ability of such coenzyme label to participate in an enzymatic reaction is affected by binding of the label conjugate with its binding partner. The rate of the resulting enzymatic reaction is measurable by conventional detectant systems to yield an ultimately detectable signal. Assay systems of this type are described in commonly assigned, copending application Ser. No. 894,836, filed Apr. 10, 1978 (corresponding to published German OLS No. 2,618,511); and in Anal. Biochem. 72:271 (1976), Anal. Biochem. 72:283 (1976) and Anal. Biochem. 76:95 (1976).

(d) Enzyme Modulator Labels

The label conjugate in this system is composed, in its label portion, of an enzyme modulating functionality such as an enzyme inhibitor or stimulator, and the ability of such modulator label to modulate the activity of an enzyme is affected by binding of the label conjugate with its binding partner. The rate of the resulting enzymatic reaction is measurable by conventional detectant systems to yield an ultimately detectable signal. Assay systems of this type are described in commonly owned U.S. Pat. No. 4,134,792.

(e) Enzyme Labels

In this system, the label is an enzyme and the activity of the enzyme label is affected by binding of the label conjugate with its binding partner. Resulting enzyme activity is measurable by conventional detectant systems to yield and ultimately detectable signal. Assay systems of this type are described in U.S. Pat. Nos. 3,817,837 and 4,043,872.

(f) Quenchable Fluorescent Labels

The label conjugate in this system is composed, in its label portion, of a fluor the fluorescence of which is quenched in some measurable degree when the label conjugate is bound by its binding partner, usually a protein such as an antibody. The fluorescent label is measured directly, with its fluorescence being the detectable signal. Assay systems of this type are described in U.S. Pat. Nos. 4,160,016 and in J. Clin. Pat. 30:526 (1977).

(g) Fluorescence Polarization Labels

The label in this system is also a fluor; however, the affected characteristic is polarization of fluorescence due to binding of the label conjugate by its binding partner, usually a protein such as an antibody. Assay systems of this type are described in J. Exp. Med. 122:1029 (1965).

(h) Chemically-Excited Fluorescent Labels

In this system, the label is again a fluor, however, the ability of the fluor label to be chemically excited to an energy state at which it fluoresces is affected by binding of the label conjugate with its binding partner. Chemical excitation of the label is usually accomplished by exposure of the fluor label to a high energy compound formed in situ. Assay systems of this type are described in commonly-owned copending application Ser. No. 4,580, filed Jan. 18, 1979, now U.S. Pat. No. 4,238,195.

(i) Double Antibody Steric Hindrance Labels

Another assay system is the double antibody immunoassay system described in U.S. Pat. Nos. 3,935,074 and 3,988,943. The label conjugate comprises two epitopes, one of which participates in the immunological reaction with the ligand and anti-ligand antibody and the other of which is bindable by a second antibody, with the restriction that the two antibodies are hindered from binding to the label conjugate simultaneously. The second epitope can be a fluor the fluroescence of which is quenched by the second antibody binding, or which may participate in an ancillary competitive binding reaction with a labeled form of the second epitope for binding to the second antibody. Various detectant systems are possible in such a system as described in the aforementioned patents. Related assay systems are described in U.S. Pat. Nos. 4,130,462 and 4,161,515 and in British Pat. No. 1,560,852.

(j) Energy Transfer Labels

In this system, the label is one member of an energy transfer donor-acceptor pair and the binding partner is conjugated with the other of such pair. Thus, when the label conjugate is bound by binding partner, the energy expression of the donor component of the pair is altered by transferance to the acceptor component. Usually, the donor is a fluor and the acceptor is a quencher therefor, which quencher may or may not be a fluor as well. In such embodiment, the detectable signal is fluorescence, but other detectant systems are possible also. Such assay systems are described in U.S. Pat. Nos. 3,996,345; 4,174,384; and 4,199,559 and in British Patent No. 2,018,424.

(k) Other Labels

Other homogeneous specific binding assay systems described in the art which can be used in the present invention include the use of such labels as:
 (i) nonenzymic catalysts, such as electron transfer agents (see U.S. Pat. No. 4,160,645);
 (ii) nonenzymic chemiluminescers (see commonly owned, copending application Ser. No. 894,836 referred to above);
 (iii) "channeling" labels (see British Pat. No. 2,018,986);
 (iv) "particle" labels (see British Patent No. 2,019,562); and
 (v) labeled liposome particles (see U.S. Pat. No. 4,193,983).

4. THE REAGENT LAYER(S)

Also provided is a method of preparing the reagent layer(s) which comprises incorporating a radiation diffusing carrier member with the components of the test system. When this incorporation is by impregnation with one or more solutions of the assay reagents according to the invention, the carrier so impregnated is then dried. In addition to impregnation, the devices of the present invention can be made by other suitable techniques such as printing or spraying the composition onto a layer of carrier material or incorporating the solutions into film forming liquids and allowing the combination so prepared to set or solidify.

Where the carrier member comprises multiple layers, e.g., paper of other fibrous material, such layers may be maintained in laminar relationship by adhesives which permit fluid passage between layers. In preparing integral analytical elements using film formers, the layer(s) can be preformed separately and laminated to form the overall element. The material of the film layer(s) can be a composition comprising a plasticizer and a polymer suitable to impart dimensional stability. Layers prepared in such a manner are typically coated from solution or dispersion onto a surface from which the dried layer can be physically stripped. However, a convenient method which can avoid problems of multiple stripping and lamination steps is to coat an initial layer on a stripping surface or a support, as desired, and thereafter to coat successive layers directly on those coated previously. Such coating can be accomplished by hand, using a blade coating device, or by machine, using techniques such as dip or bead coating. If machine coating techniques are used, it is often possible to coat adjacent layers simultaneously using hopper coating techniques well known in the preparation of light sensitive photographic films and papers.

Blush polymer layers can be used as the film layer material. The film is formed on a substrate by dissolving a polymer in a mixture of two liquids, one of which is of a lower boiling point and is a good solvent for the polymer and the other of which is of a higher boiling point and is a nonsolvent or at least a poor solvent for the polymer. Such a polymer solution is then coated on the substrate, and dried under controlled conditions. The lower boiling solvent evaporates more readily and the coating becomes enriched in the liquid which is a poor solvent or nonsolvent. As evaporation proceeds, under proper conditions, the polymer forms as a porous layer. Many different polymers can be used, singly or in combination, for preparing porous blush polymer layers for use in this invention. Typical examples include polycarbonates, polyamides, polyurethanes and cellulose esters, such as cellulose acetate. For layers such as those containing a label conjugate or other reagent, a coating solution or dispersion including the matrix and incorporated active materials can be prepared, coated as discussed herein and dried to form a dimensionally stable layer.

The thickness of any layer and its degree of permeabilty are widely variable and depend on actual usage. Dry thicknesses of from about 5 microns to about 100 microns have been convenient, although more widely varying thickness may be preferable in certain circumstances. For example, if comparatively large amounts of interactive material, e.g., polymeric materials like enzymes, are required, it may be desirable to prepare slightly thicker layers.

It can be advantageous to incorporate one or more surfactant materials, such as anionic and nonionic surfactant materials, in the reagent layer(s). They can, for example, enhance coatability of layer formulations and enhance the extent and range of wetting in layers that are not easily wetted by liquid samples in the absence of an aid such as a surfactant. It can also be desirable to include materials that can render nonactive in the analysis of choice, by chemical reaction or otherwise, materials potentially deleterious to such analysis.

Following are descriptions of some preferred approaches to preparation of the reagent layer(s):

(a) Miltilayer Approach

This approach relates to a method for preparing the reagent layer of a homogeneous specific binding assay element for determining a ligand in or the ligand binding capacity of a liquid sample by incorporating a carrier with a composition which includes a label conjugate, comprising a label component coupled to a ligand moiety or a specific binding analog thereof, and a reagent interreactive with the label conjugate, which method comprises (a) impregnating a carrier with a first solution of the reagent interreactive with the label conjugate in a solvent and drying the carrier; and (b) impregnating the carrier of (a) with a solution of the label conjugate in a solvent effective to prevent interreaction with the reagents of the first solution and drying the carrier. The interreactive reagent can comprise, for example, a specific binding partner for the ligand or a specific binding partner for the ligand and a component which is interreactive with the label conjugate to cleave the label component from the ligand moiety or specific binding analog thereof.

For example, a layer of carrier material is impregnated with a first solution or suspension of reagents in a first solvent and dried. Thereafter, the carrier material is impregnated with a second solution or suspension of the remaining reagents in a second solvent with prevents interaction with reagents impregnated by the first solvent and dried. In this way, the reagents in the respective solutions are incapable of substantial interreaction during preparation of the test device and thus do not react prematurely. In a preferred embodiment, certain first reagents are incorporated with a layer of carrier material using an aqueous dip. For the remaining reagents, suitable organic solvent is used such as toluene, acetone, chloroform, methylene chloride, n-propanol and ethylene dichloride. This layer is set by allowing the organic solvent to evaporate.

An example of this preferred embodiment is a method for preparing a homogeneous specific binding assay device for determining a ligand in or the ligand binding capacity of a liquid sample by incorporating a carrier with a composition which includes a β-galactosyl-umbelliferone-ligand or ligand analog conjugate, β-galactosidase, and antisera to the ligand which method comprises (a) impregnating a carrier with an aqueous solution of β-galactosidase and antisera to the ligand and drying the carrier and (b) impregnating the carrier of (a) with an acetone solution of β-galactosyl-umbelliferone-ligand or ligand analog conjugate and drying the carrier.

(b) Multizone Reagent Layer

A multizone reagent layer is prepared by (a) incorporating a first or overlaying zone with some, but less than all, of the reagents of the specific binding assay system used, (b) incorporating a second or underlaying zone with the remaining reagents, (c) setting, such as by drying, the individual zones, and (d) fixing them into laminar relationship with one another. When absorbent carrier materials are used, these reagent layers are prepared by impregnating individual layers as the zones, and drying the layers so impregnated.

The first layer and second layer each have a pair of opposite surfaces. One surface of the first layer is in laminar relationship with one surface of the second layer, sample being applied to the other surface of either of said layers. Reference to a laminar relationship connotes the ability of a fluid, whether liquid or gaseous, to pass between superposed surfaces of such layers. Such layers can be continguous or separated by intervening layers. Any intervening layer should not prevent passage between all layers.

(c) Freeze Drying Approach

This approach consists of a procedure to incorporate and prevent reaction between incompatible reagents in a single layer analytical element. When using, for example, absorbent carrier materials, a first group of reagents is incorporated with the layer material by freeze drying or at elevated temperature and the treated layer is set. The second group of reagents containing any which will react, under ambient conditions, with the first group, are applied and the element is rapidly frozen. Freezing prevent premature reaction and the subsequent removal of water by freeze drying prevents premature reaction when the layer is brought back to room temperature.

In the preferred embodiment, one group of reagents can be added in aqueous solution to a layer and dried. The addition of a second group of reagents in aqueous solution is followed by rapid freezing and then freeze drying to remove water. This procedure allows the incorporation of and prevents the interaction between some reagents which are only water soluble. In addition, it avoids the use of organic solvents, certain of which may interact deleteriously with some reagents (e.g., enzymes).

The procedure permits formulation of elements utilizing homogeneous specific binding assay reagents in which all reagents are provided within a single layer element.

(d) Preformed Complex Approach

Competition between sample ligand and labeled ligand for binding to a binding partner (here exemplified by an antibody-"Ab") can be summarized by the equation:

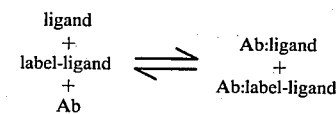

In the system illustrated above, the antibody and the label conjugate are kept separate until the introduction of the sample. This embodiment of the described invention makes use of the reverse reaction and reequilibration with the ligand as shown by the equation below:

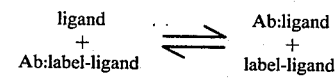

where the amount of displaced label conjugate is related to the sample ligand concentration. The advantage is that all reagent components can be combined in one incorporation medium to provide a system that requires only the addition of sample to be tested.

As such, this approach provides a method of preparing the reagent layer of a homogeneous specific binding assay device for determining a ligand in a liquid sample, which method comprises (a) forming a complex between a label conjugate, the conjugate comprising a label component coupled to the ligand or a specific binding analog thereof, and a specific binding partner for the ligand; and (b) incorporating a carrier with the complex. In this method, forming the complex can comprise associating the label conjugate and specific binding partner therefor and allowing the conjugate, the binding partner and the complex to reach a state of equilibrium.

More particularly, the layers are prepared by incubating a given conjugate with its respective antisera for a short period, such as 15 minutes. Then, any additional reagents are added and the system allowed to incubate an additional period. The solution so formed is impregnated into or otherwise incorporated with a layer of carrier material which is then allowed to set.

5. THE SUPPORT LAYER

As mentioned previously herein, the integral analytical elements include a support. The support can be opaque, translucent or transparent to light or other energy. A support of choice for any particular element will be selected independently of the intended mode of signal detection. Preferred supports include those of polystyrene or similar plastics.

6. MULTILAYER ELEMENT PREPARATION

Further in accordance with the invention there is provided a method for the preparation of a multilayer analytical element for the detection of a ligand in or the ligand binding capacity of a liquid sample of the type having a reagent layer incorporating reagents which are responsive to the ligand in or the ligand binding capacity of the sample to give a detectable response, a radiation blocking layer, and a support layer, each such layer having opposed surfaces, which method comprises the steps of: (1) fixing a surface of the support layer to a surface of a radiation nondiffusing reflecting layer which is (a) impermeable to the ligand, reagents of the reagent layer, and products of their interreaction; and (b) inert to the ligand, reagents of the reagent layer, and products of their interreaction; and (2) fixing a surface of a radiation diffusing reagent layer to the opposed surface of the radiation reflecting layer.

In one embodiment, fixing a surface of the support layer to a surface of the radiation reflecting layer comprises forming the radiation reflecting layer on the surface of the support layer. In another embodiment, fixing a surface of the support layer to a surface of the radiation reflecting layer comprises forming the radiation reflecting layer and, thereafter, fixing a surface of the radiation reflecting layer so forming to a surface of the support layer.

7. DETECTABLE RESPONSE

As previously noted, many of the recently devised homogeneous specific binding assay systems provide, or can be readily adapted to provide, a detectable response such as a color change, chemiluminescence, or fluorescence related to the presence or amount of the ligand under assay in the liquid sample.

The terms "detectable species" and similar terms as used herein, refer to atoms, chemical groups (i.e., a portion of a molecule) or chemical compounds that are themselves directly or indirectly detectable and the term "detectable response", and similar terms as used herein, refer to the detectable manifestation of the presence of such species. Examples are electromagnetic radiation signals such as fluorescence, phosphorescense, chemiluminescence, a change in light absorption, or reflectance in the visible spectrum thereby producing a visible color change, a change in light absorption or reflectance outside the visible range such as in the ultraviolet range or infrared range. As will be apparent to one skilled in the art the phrase "detectable response", as used herein, is intended in its broadest sense. In addition to electro-magnetic radiation signals the term "detectable response" is also meant to include any observable change in a system parameter, such as a change in or appearance of a reactant, observable precipitation of any component in the test sample or a change in any other parameter, whether it be in the reagent system or the test sample. Such other detectable responses include electrochemical responses and calorimetric responses. Moreover, the detectable response is one which can be observed through the sensor directly or by use of ancillary detection means, such as a spectrophotometer, ultraviolet light-sensing equipment, fluorometer, spectrofluorometer, pH meter and other sensing means. Desirably, such detectability can be conveniently imparted to the full amount of detectable species without affecting the amount of diffusible product resulting from the analyte interactions which are the basis of the intended analysis.

After the analytical result is obtained as a detectable change, it is measured, usually by passing the test element through a zone in which suitable apparatus for reflection, transmission or fluorescence photometry is provided. Such apparatus serves to direct a beam of energy, such as light. The light is then reflected from the element back to a detector. The analytical result is detected in a region of the element totally within the region in which such result is produced. Use of reflection spectrophometry can be advantageous in some situations as it effectively avoids optical interference from any residues, such as blood cells or urine sediment, which have been left on or in the layers of the element or from a typical urine colors. Conventional techniques of fluorescence spectrophotometry can also be employed. Generally, electromagnetic radiation in the range of from about 200 to about 900 nanometers (nm) has been found useful for such measurements, although any radiation to which the reagent layer(s) is permeable and which is capable of quantifying the product produced in the element can be used. Various calibration techniques can be used to provide a control for the analysis. As one example, a sample of a standard solution of the ligand under assay can be applied adjacent to the area where the drop of sample is placed in order to permit the use of differential measurements in the analysis.

EXAMPLES

The following examples describe experiments which were performed in developing the present invention. While they illustrate preferred embodiments, they are in no way to be interpreted as limiting the scope of the invention.

EXAMPLE I

Comparison of Model Systems

In order to evaluate the effect of the reflecting layer of the invention, elements were prepared both with and without the described reflecting layer between the reagent layer and support layer. The reagent layer in this model system is provided with a reagent solution which, itself, emits a detectable response, fluorescence. Therefore, this example encompasses a comparison which is not limited to any particular ligand.

Conjugate Preparation $\beta$-galactosyl-umbelliferone-labeled theophylline conjugates are prepared according to the reaction scheme shown in FIG. 1. This synthetic route is exemplified by the following method of preparing 8-[3-(7-$\beta$-galactosyl-coumarin-3-carboxamido)propyl] theophylline (4), $n=3$.

8-(3-Aminopropyl)theophylline (2)

A mixture of 2.66 grams (g) (0.01 mol) of 8-(3-carboxypropyl)theophylline (1) [Cook et al, Res. Commun. Chem. Path. Pharmacol. 13(3): 497–505 (1976)], 20 milliliters (ml) of chloroform, and 3 ml of concentrated sulfuric acid was stirred at 50° C. under an argon atmosphere. To this was added 1.3 g of solid sodium azide portionwise over a 90 minute period [cf. Organic Reactions 47:28 (1967)]. The reaction was cooled and the solvent removed under reduced pressure. The residue was combined with enough sodium bicarbonate solution to bring the pH to 7.5. Ten grams of celite (Fisher Scientific Co., Pittsburgh, Pennsylvania) was added and the water evaporated. The impregnated celite was placed atop a column of 200 g of silica gel (E. Merck Co., Darmstadt, West Germany) made up in 9:1 (v:v) ethanol—1 molar aqueous triethylammonium bicarbonate. The column was eluted with this solvent and 15 ml fractions were collected. Fractions 171 to 225 were combined and evaporated to give 500 milligrams (mg) of a white powder. This substance was rechromatographed on a column of CM-Sephadex, ammonium form (Pharmacia Fine Chemicals, Piscataway, N.J., USA), eluting with 0.5 molar ammonium bicarbonate. The bed volume was 3 cm by 50 cm; and 10 ml fractions were collected. Fractions 65 to 110 were combined and evaporated to give 250 mg of a white solid. It was taken up in dilute hydrochloric acid, then reevaporated.

The residue was recrystallized from methanol to give 90 mg (3% yield) of the hydrochloric acid salt of (2) as pale tan needles that did not melt below 300° C.

Analysis: Calculated for $C_{10}H_{16}N_5Cl0_2$: C, 43.88; H, 5.89; N, 25.59. Found: C, 43.77; H, 5.88; N, 25.46. Infrared Spectrum (KCl): 1695 $cm^{-1}$ and 1655 $cm^{-1}$ (amide carbonyls).

8-[3-(7-$\beta$-galactosylcoumarin-3-carboxamido)propyl]-theophylline (4).

A reaction mixture was prepared containing 24 g of potassium hydroxide, 80 ml of water, 240 ml of methanol and 20 g (0.035 mmol) of ethyl 7-$\beta$-galactosylcoumarin-3-carboxylate [Burd et al, Clin. Chem. 23:1402 (1977)]. The reaction was stirred at 50° C. for 15 hours. When cool, the methanol was removed under reduced pressure. The concentrated aqueous solution as acidified to pH 2.0 with concentrated hyrochloric acid. The white precipitate was collected, washed with cold water, and recrystallized from hot water. The crystals were collected, washed with acetone, and dried at 80° C. for 1 hour. This gave 12 g of 7-$\beta$-galactosylcoumarin-3-carboxylic acid as white crystals, mp 250°-255° C.

A mixture of 1.45 g (0.004 mol) of 7-$\beta$-galactosylcoumarin-3-carboxylic acid, 404 mg (0.004 mol) of triethylamine, and 40 ml of dry dimethyl formamide (DMF) was cooled to −10° C. while stirring under argon. To this was added 546 mg (0.004 mol) of isobutyl chloroformate (Aldrich Chemical Co., Milwaukee, Wisconsin) to form the mixed anhydride ($\beta$). Ten minutes later, an additional 404 mg of triethylamine and 949 mg (0.004 mol) of 8-(3-aminopropyl) theophylline (2) was added to the flask. After stirring for 30 minutes at −10° C., the reaction was allowed to warm to room temperature. It was combined with 10 g of silica gel and the DMF removed under high vacuum. The impregnated silica gel was placed atop a column of 170 g of silica gel and the column eluted with anhydrous ethanol and collecting 15 ml fractions. Fractions 41 to 475 were combined and evaporated to give 545 mg of a yellow solid. It was dissolved in water, filtered, and concentrated to a 20 ml volume. A small amount of precipitate formed and was discarded. The filtrate was chromatographed on a 2.5 cm by 57 cm column of Sephadex LH-20 gel (Pharmacia Fine Chemicals, Piscataway, New Jersey), eluting with water and collecting 15 ml fractions. Fractions 18 to 23 were combined, evaporated, and residue recrystallized from water to give 55 mg (2% yield) of the label conjugate (4) as a light yellow solid, mp 190°-192° C.

Analysis: Calculated for $C_{26}H_{29}N_5O_{11}$: C, 53.15; H, 4.98; N, 11.92. Found: C, 52.65; H, 5.01; N, 11.80.

The above-described synthesis of the $\beta$-galactosylcoumarin-theophylline conjugate (4), n=3, can be modified to yield label conjugates wherein n=2 through 6 by replacing the starting material 8-(3-carboxypropyl)-theophylline (1), n=3, with the appropriate 8-($\omega$-carboxyalkyl)theophylline as follows:

| n | Alkylene |
|---|----------|
| 2 | ethylene |

-continued

| n | Alkylene |
|---|----------|
| 4 | butylene |
| 5 | pentylene |
| 6 | hexylene |

Preparation of Theophylline Umbelliferone (TU) Fluor

TU was prepared by incubating 32 micromolar ($\mu$M) theophylline umbelliferfone-galactose in a solution containing 1.6 units per milliliter (U/ml) $\beta$-galactosidase in 0.05 molar (M) bicine buffer (pH 8.5) for 3 hours at room temperature.

Application of TU Fluor to Paper

Figure 2:
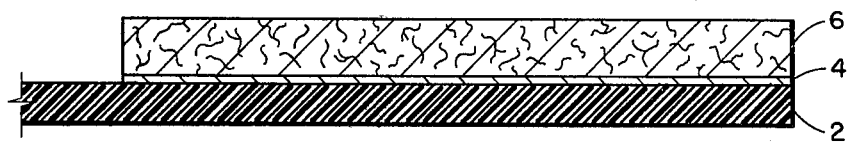
FIG. 2 is a cross-section view of an analytical element of the invention as described in Example I.

Referring to FIG. 2, aliquots of 20 microliters ($\mu$l) of 15.6 micromolar ($\mu$M) TU fluor in 0.05 M bicine buffer (pH 8.5) were applied to two groups of 1 centimeter (cm) ×1 cm paper segments 6. One group had been mounted by double-faced adhesive tape (not shown) to a polystyrene support layer 2. To form elements according to the invention, the other group of papers segments 6 were mounted onto the surface of a Mylar (3M) layer 4 which was then fixed by double-faced adhesive tape (not shown) to a polystyrene support 2. To compare these devices, a front face fluorescence measurement was performed in an SLM 8000 spectrofluorometer (SLM Instruments, Inc. Urbana, Ill.) using vertically mounted strips. The excitation source was 60° to the normal to the paper 6 and the emission detector was 30° to the normal to the device. The fluorescence response is measured (in arbitrary units) for a buffer blank (0.05 M bicine, pH 8.5) or the TU fluor. The fluorescence responses of TU fluor on various papers, with and without Mylar backing, are summarized in Table I.

TABLE I

| Paper | Fluorescence | |
|---|---|---|
| | Buffer | TU fluor |
| No Mylar | | |
| Whatmann 3MM | 90 | 1472 |
| Whatmann 31ET | 106 | 2765 |
| Mylar | | |
| Whatmann 3MM | 24 | 2753 |
| Whatmann 3ET | 44 | 4914 |

As shown in Table I, introduction of the reflecting layer dropped the buffer background signal. In addition it produced an appreciable enlargement in the fluorescence signal produced by the fluor applied to paper.

EXAMPLE II

Measurement of enzymatic reaction on Whatman 3MM paper using fluorescence detection 1 cm ×1 cm Whatman 3MM pads were impregnated with 0.96 I.U. $\beta$-galactosidase in a 0.1 M bicine buffer (pH 8.5) solution. Reaction was initiated by the application of 40 $\mu$l of 8 $\mu$M theophylline-umbelliferone-galactose and the development of the fluorescence signal was measured as described in Example I.

Figure 3:
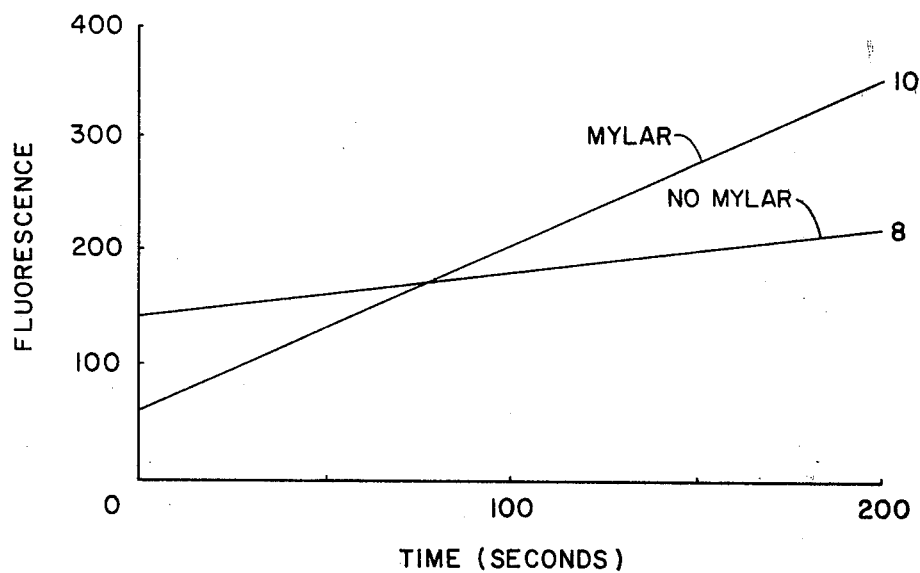
FIGS. 3-4 are graphical representations of data obtained from the experiments described in Examples I and III, respectively.

The time dependent response is shown in FIG. 3 for Whatman 3MM paper with 10 or without Mylar backing 8. Again, a lower initial background signal is observed in paper having the Mylar backing. In addition, the increase in fluorescence signal with time is greater on paper with Mylar backing.

EXAMPLE III

Measurement of enzymatic reactions on Whatman ET 31 paper using fluorescence detection Paper pads were prepared as in Example II, except using Whatman 31 ET paper. The reaction was initiated by the application of 60 μl of 5.33 μM theophyllineumbelliferone-galactose and the fluorescent signal was measured as previously described.

Figure 4:
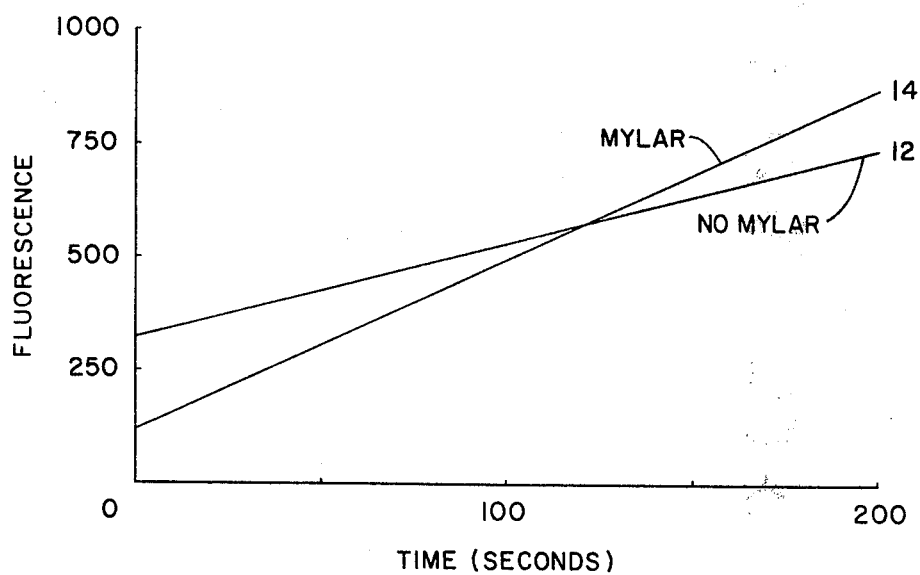

The time dependent response is shown in FIG. 4 for Whatman 31 ET paper with 14 or without Mylar backing 12. Again a lower initial background signal is observed in paper having the Mylar backing. In addition, the increase in fluorescence signal with time is greater on paper with Mylar backing.

EXAMPLE IV

Phenobarbital Immunoassay on Devices with or without reflective Mylar backing

Phenobarbital [5-ethyl-5-phenylbarbituric acid, cf. The Merck Index, 9th ed., p. 939(1976)], sold under various trademarks including Luminal, is an anticonvulsant drug useful in the management of epilepsy. In most patients, the therapeutic range of serum concentration lies between 15 and 40 μg/ml whereas toxicity almost invariably appears at blood levels over 50 μg/ml.

Conjugate Preparation

This synthetic route is exemplified by the following method of preparing 5-[4-(7-β-galactosylcoumarin-3-carboxamido)butyl]-5-phenylbarbituric acid n=4.

Diethyl 2-Carbethoxy-2-phenylpimelate

A 50% mineral oil dispersion of 2.4 g (0.1 mol) of sodium hydride was placed in a 500 ml, 3-neck round bottom flask under an argon atmosphere. It was washed free of oil with 250 ml of dry hexane and combined with 23.6 g (0.1 mol) of diethyl phenylmalonate (Aldrich Chemical Co., Milwaukee, WI) dissolved in 100 ml of dry dimethylformamide (DMF). The mixture was stirred at room temperature for 15 minutes, during which time hydrogen evolution ceased. A solution of 20.9 g (0.1 mol) of ethyl 5-bromopentanoate (Aldrich Chemical Co., Milwaukee, WI) in 100 ml of dry DMF was added and the reaction stirred over-night at 70° C. Removal of the DMF on a rotary evaporator at 50° C./0.3 mm left an oily residue that was partitioned between 300 ml of water and 500 ml of water, 200 ml of saturated sodium chloride solution, and dried over anhydrous magnesium sulfate. It was filtered and evaporated to give an oil that was chromatographed on 1500 g of silica gel (E. Merck Co., Darmstadt, West Germany). The column was eluted with chloroform and 20 ml fractions were collected.

Fractions 771 to 1200 were combined and evaporated to give an oil that was evaporatively distilled at 160° C./0.01 mm to yield 28 g (77% yield) of the desired product as a white oil.

Analysis: Calculated for $C_{20}H_{28}O_6$: C, 65.91; H, 7.74. Found: C, 65.90; H, 7.75. Infrared Spectrum (neat): 1735 cm$^1$ (carbonyl).

5-(4-Carbethoxybutyl)-5-phenyl-2-thiobarbituric Acid and 5-(4-Carboxybutyl)-5-phenylbarbituric Acid A solution of 3.68 g (0.16 g-atm) of sodium and 15.2 g (0.2 mol) of thiourea in 100 ml of ethanol was refluxed while stirring under an argon atmosphere. To this was added, dropwise over 30 minutes, 28 g (0.08 mol) of diethyl 2-carbethoxy-2-phenylpimelate. After refluxing for 6 hours, the reaction was cooled and concentrated on a rotary evaporator. The residue was taken up in 200 ml of water and extracted with 200 ml of ethyl acetate followed by 200 ml of ether. The aqueous phase was acidified to pH 1 which caused the precipitation of a heavy yellow oil. This oil was chromatographed on 850 g of silica gel. The column was eluted with 9:1 (v:v) toluene: ethanol and 20 ml fractions were collected.

Fractions 45 to 63 were combined, evaporated to dryness, and the solid residue recrystallized from aqueous ethanol. This gave 5 g (18% yield) of the thiobarbituric acid as pale yellow cyrstals, mp 121° C.

Analysis: Calculated for $C_{17}H_{26}N_2SO_4$: C, 58.60; H, 5.79; N, 8.04. Found: C, 58.42; H, 5.82; N, 8.07. Infrared Spectrum (KCl): 1735 cm$^{-1}$ (carbonyl); 1675 cm$^{-1}$ (carbonyl).

Fractions 64 to 100 were combined and evaporated to give 6 g of slightly impure. This was taken up in 50 ml of dimethyl sulfoxide containing 1 ml of concentrated sulfuric acid and heated on the stream bath for 3 hours. [Mikolajczyk and Luczak, Chem. Ind. 77 (1972)]. When cool, the dimethyl sulfoxide was removed under high vacuum. To the residue was added 25 ml water and 25 ml of dioxane and the solution heated on the steam bath for 2 hours. Removal of the solvent gave a dark residue that was partitioned between 200 ml of ether and 200 ml of aqueous sodium bicarbonate solution. The aqueous phase was filtered and neutralized with hydrochloric acid. A solid precipitated that was recrystallized from aqueous ethanol to give 1.9 g (36% yield) of the barbituric acid as white crystals, mp 202°–203° C.

Analysis: Calculated for $C_{15}H_{16}N_2O_5$: C, 59.20; H, 5.30; N, 9.21. Found: C, 58.65; H, 5.34; N, 9.25. NMR Spectrum ($C_5D_5N$); δ1.9 (m, 4H); δ2.6 (m, 4H); δ7.3 (m, 3H); δ7.8 (m, 2H).

5-(4-Aminobutyl)-5-phenylbarbituric Acid

A mixture of 15 ml of concentrated sulfuric acid, 7 g (0.023 mol) of barbituric acid and 3.45 g (0.053 mol) of sodium azide was placed in a small, stainless steel stirring autoclave and heated to 60° C. After 90 minutes the autoclave was cooled, opened, and the black suspension rinsed out with 300 ml of water and neutralized with solid sodium bicarbonate. It was combined with 50 g of celite (Fisher Scientific Co., Pittsburgh, Pa.) and the water removed on a rotary evaporator. This left a dirty gray mass that was air dried, then ground to a fine consistency in a mortar. It was placed atop a 250 g column of silica gel made up in 9:1 (v:v) ethanol: 1 M aqueous triethylammonium bicarbonate. The column was eluted with this solvent and 20 ml fractions were collected.

Fractions 73 to 107 were combined and evaporated to give a solid residue. It was taken up in dilute hydrochloric acid, evaporated to dryness, and this residue recrystallized from ethanol to give 1.75 g (24% yield) of the hydrochloride salt of 5-(4-aminobutyl)-5-phenylbarbituric acid as find white needles that did not melt below 280° C.

Analysis: Calculated for $C_{14}H_{17}N_3O_3 \cdot HCl$: C, 53.93; H, 5.82; N, 13.48. Found: C, 53.44; H, 5.94; N, 13.29. Infrared Spectrum (KCl): 1710 cm$^{-1}$ (carbonyl).

5-[4-(7-β-Galactosylcoumarin-3-carboxamido)butyl]-5-phenylbarbituric Acid

A mixture of 737 cm (2 mmol) of 7-β-galactosylcoumarin-3-carboxylic acid [Burd et al, Clin. Chem. 23:1402 (1977)], 0.278 ml (202 mg, 2 mmol) of triethylamine, and 25 ml of dimethylformamide was cooled to −5° C. in a methanol-ice bath while stirring under an argon atmosphere. To this was added 273 mg (2 mmol) of the amine was added. The reaction was stirred at −5° C. for 2 hours, then allowed to warm to room temperature overnight. Eight grams of silica gel was added and the solvent removed on a rotary evaporator under high vacuum. The impregnated silica gel was placed atop a column of 200 g of silica gel made up in ethyl acetate. The column was eluted with a gradient of 2 liters (L) of ethyl acetate to 2 L of 1:1 (v:v) ethyl acetate:ethanol and 15 ml of fractions were collected.

Fractions 126 to 175 were combined and evaporated to give 750 mg (80% yield) of the desired conjugate as a white solid, mp 161°–163° C.

Analysis: Calculated for $C_{30}H_{31}N_3O_{12}$: C, 57.60; H, 4.99; N, 6.72. Found: C, 57.54; H, 5.29; N, 6.27.

Infrared Spectrum (KCl): 1710 cm$^{-1}$ (carbonyl).

Optical Rotation: $[\alpha]_D = -45.58°$ (cl. 0, $CH_3OH$).

Mass Spectrum (field desorption): m/e 626 [p+1].

The above-described synthesis of the β-galactosyl-coumarin-phenobarbital conjugate (n=4) can be modified to yield label conjugates wherein n=2 through 6 by replacing the starting material ethyl 5-bromopentanoate with the appropriate ethyl ω-bromoalkanoate as follows:

| n | alkylene |
|---|----------|
| 2 | ethylene |
| 3 | propylene |
| 5 | pentylene |
| 6 | hexylene |

Preparation of the Elements

Sheets of Whatman 31 ET paper were impregnated to saturation with a solution containing:

| Component | Quantity |
|-----------|----------|
| phenobarbital antisera | 40% (v/v) |
| Bicine buffer, pH 9.0 | 0.6 M |
| β-galactosidase | 6100 IU/L |

The paper so impregnated was then dried at 50° C. This impregnated paper was then impregnated with a solution containing 11.9 μM/liter of conjugate in acetone and again dried at 50° C.

One group of papers was mounted on reflective Mylar, then the other surface of the Mylar layer was fixed, by double-faced adhesive tape, onto a polystyrene substrate and cut into 0.5 cm wide strips (element dimensions are 0.5×1 cm mounted on 0.5×8.3 cm polystyrene handle). Another group of papers was prepared as above except that no reflective Mylar layer was included, i.e. the reagent containing paper was fixed directly to the polystyrene support.

Analytical Procedure

The analytical elements which had been prepared and fixed to supports as described above were each inserted into a mechanical holder suitable for horizontally positioning the device in a filter fluorometer which was made by Ames Company, a division of Miles Laboratories, Inc., Elkhart, Ind. Excitation light at 405 nm was provided at 90° angle to the surface and collection of light at 90° was performed at 450 nm. Aliquots of 35 μl containing specified levels of phenobarbital and 5% human serum in 0.05 M bicine buffer (pH 8.5) were applied to the paper. The fluoroscence signal was measured after 2 minutes of reaction.

Results

The results of this experiment are shown in Table II.

TABLE II

| Phenobarbital (μg/ml) | Fluorescence | |
|---|---|---|
|  | No Mylar | Mylar |
| 0 | 0.133 | 0.115 |
| 0.25 | 0.145 | 0.126 |
| 0.5 | 0.158 | 0.157 |
| 1.0 | 0.203 | 0.260 |
| 2.0 | 0.251 | 0.316 |
| 3.0 | 0.308 | 0.472 |
| Range (0–3 μg/ml): | 0.175 | 0.357 |

Conclusion

The introduction of the Mylar backing is shown to reduce the fluorescence (background) at zero level and to increase the fluorescence signal due to product generation in the test. The overall range of the fluorescence response is appreciably increased.

What is claimed is:

1. In a multilayer analytical element for detecting a ligand in or the ligand binding capacity of a liquid sample of the type having at least one reagent layer incorporating reagents which are responsive to the ligand in or the ligand binding capacity of the sample to give a detectable response, a radiation reflecting layer, and a support layer, the improvement wherein at least one reagent layer is a radiation diffusing layer and the radiation reflecting layer is a radiation nondiffusing reflecting layer which is (a) interposed between the at least one reagent layer and the support layer; (b) impermeable to the ligand, reagents of the at least one reagent layer, and products of their interreaction; and (c) inert to the ligand, reagents of the at least one reagent layer, and products of their interreaction.

2. The multilayer analytical element of claim 1 wherein the radiation reflecting layer comprises a radiation impermeable mirrored surface.

3. The multilayer analytical element of claim 2 wherein the radiation reflecting layer comprises a coating of reflective material on the support layer.

4. The multilayer analytical element of claim 2 where the radiation reflecting layer comprises a metal electrocoating on the support layer.

5. The multilayer analytical element of claim 2 wherein the radiation reflecting layer comprises a metal foil.

6. The multilayer analytical element of claim 2 wherein the radiation reflecting layer comprises a polymeric material incorporated with a metal.

7. The multilayer analytical element of claim 2 wherein the radiation reflecting layer comprises a metalized polyester tape.

8. The multilayer analytical element of claim 1 wherein a reagent layer comprises:

(a) reagents for a homogeneous specific binding assay system which produces a detectable response that is a function of the presence of the ligand in or the ligand binding capacity of the sample; and (b) a solid carrier incorporated with the reagents of (a).

9. The multilayer analytical element of claim 8 wherein reagents for the homogeneous specific binding assay which are interreactive are physically separated prior to use of the element.

10. The multilayer analytical element of claim 8 wherein the homogeneous specific binding assay system includes a label which participates in an enzymatic reaction.

11. The multilayer analytical element of claim 10 wherein the label is a substrate for an enzyme.

12. The multilayer analytical element of claim 11 wherein the enzyme is capable of acting on the substrate label to produce a detectable product.

13. The multilayer analytical element of claim 10 wherein the label is a prosthetic group of an enzyme.

14. The multilayer analytical element of claim 13 wherein the prosthetic group is capable of combining with an apoenzyme to form the enzyme.

15. The multilayer analytical element of claim 10 wherein the label is an enzyme.

16. The multilayer analytical element of claim 1 wherein a reagent layer comprises:
(a) a reagent composition including
(i) an antibody which binds the ligand,
(ii) a conjugate of the ligand, or a binding analog thereof, and a label; and
(iii) a detectant system which interacts with the label to produce a detectable response that is different when the label conjugate is bound by the antibody compared to when it is not so bound, whereby the detectable response is a function of the presence of the ligand in the liquid sample; and
(b) a solid carrier incorporated with the reagent composition.

17. The multilayer analytical element of claim 16 wherein the detectant system involves an enzymatic chemical reaction in which the label is a participant.

18. The multilayer analytical element of claim 17 wherein the label is a substrate for an enzyme and wherein the detectant system comprises the enzyme.

19. The multilayer analytical element of claim 18 wherein the enzyme acts on the substrate-labeled conjugate to produce a detectable product.

20. The multilayer analytical element of claim 17 wherein the label is a prosthetic group of an enzyme and the detectant system comprises an apoenzyme which combines with the prosthetic group to form the enzyme.

21. The multilayer analytical element of claim 20 wherein the detectant system additionally comprises an indicator for the activity of the enzyme.

22. The multilayer analytical element of claim 20 wherein the label is flavin adenine dinucleotide and the apoenzyme is apoglucose oxidase.

23. The multilayer analytical element of claim 22 wherein the detectant system additionally comprises an indicator for glucose oxidase activity.

24. The multilayer analytical element of claim 23 wherein the indicator comprises glucose, peroxidase, and a substance which produces a chromogenic response to hydrogen peroxide.

25. The multilayer analytical element of claim 17 wherein the label is an enzyme and the detectant system comprises an indicator for the activity of the enzyme.

26. In a multilayer analytical element for detecting a ligand in or the ligand binding capacity of a liquid sample of the type having a reagent layer incorporating reagents which are responsive to the ligand in or the ligand binding capacity of the sample to give a detectable response, a radiation reflecting layer, and a support layer, the improvement wherein:
(1) the reagent layer comprises
(a) reagents for a homogeneous specific binding assay system which produces a detectable response that is a function of the presence of the ligand in or the ligand binding capacity of the sample; and
(b) a solid carrier incorporated with the reagents; and
(2) the radiation reflecting layer comprises a radiation impermeable reflective metallic layer which layer is:
(a) interposed between the reagent layer and the support layer;
(b) impermeable to the ligand, reagents of the reagent layer, and products of their interreaction; and
(c) inert to the ligand, reagents of the reagent layer, and products of their interreaction.

27. In a multilayer analytical element for the detection of a ligand in or the ligand binding capacity of a liquid sample of the type having a reagent layer incorporating reagents which are responsive to the ligand in or the ligand binding capacity of the sample to give a detectable response, a radiation reflecting layer, and a support layer, the improvement wherein:
(1) the reagent layer comprises
(a) reagents for a homogeneous specific binding assay system which produces a detectable response that is a function of the presence of the ligand in or the ligand binding capacity of the sample; and
(b) a solid carrier which comprises a plurality of zones, each of which zones is incorporated with a different reagent or reagent combination of the homogeneous specific binding assay system; and
(2) the radiation reflecting layer comprises a radiation impermeable reflective metallic layer which layer is
(a) interposed between the reagent layer and the support layer;
(b) impermeable to the ligand, reagents of the reagent layer, and products of their interreaction; and
(c) inert to the ligand, reagents of the reagent layer, and products of their interreaction.

28. In a multilayer analytical element for the detection of a ligand in or the ligand binding capacity of a liquid sample of the type having a reagent layer incorporating reagents which are responsive to the ligand to give a detectable response, a radiation reflecting layer, and a support layer, the improvement wherein:
(1) the reagent layer comprises
(a) a reagent composition including
(i) an antibody which binds the ligand,
(ii) a conjugate of the ligand or a binding analog thereof, and a label, and
(iii) a detectant system which interacts with the label to produce a detectable response that is different when the label conjugate is bound by the antibody compared to when it is not so bound, whereby the detectable response is a function of the presence of the ligand in the liquid sample, and (b) a solid carrier incorporated with said reagent composition; and (2) the radiation reflecting layer comprises a radiation impermeable reflective metallic layer which layer is
   (a) interposed between the reagent layer and the support layer;
   (b) impermeable to the ligand, reagents of the reagent layer, and products of their interreaction; and
   (c) inert to the ligand, reagents of the reagent layer, and products of their interreaction.

29. In a multilayer analytical element for the detection of phenobarbital in a liquid sample of the type having a reagent layer incorporating regents which are responsive to phenobarbital to give a detectable response, a radiation reflecting layer, and a support layer, the improvement wherein:

(1) the reagent layer comprises:
   (a) reagents for a homogeneous specific binding assay system which produces a detectable response that is a function of the presence of phenobarbital in or the phenobarbital binding capacity of the sample; and
   (b) a solid carrier incorporated with the reagents; and (2) the radiation reflecting layer comprises a radiation impermeable reflective metallic layer which layer is:
   (a) interposed between said reagent layer and said support layer;
   (b) impermeable to phenobarbital, reagents of the reagent layer, and products of their interreaction; and
   (c) inert to phenobarbital, reagents of the reagent layer, and products of their interreaction.

* * * * *